(12) United States Patent
Hancock et al.

(10) Patent No.: US 11,964,067 B2
(45) Date of Patent: Apr. 23, 2024

(54) STERILIZATION APPARATUS

(71) Applicant: CREO MEDICAL LIMITED, Chepstow (GB)

(72) Inventors: Christopher Paul Hancock, Bath (GB); Morgan Bryant, Chepstow (GB); Louis Turner, Chepstow (GB); Sandra Swain, Chepstow (GB); Julian Mark Ebbutt, Chepstow (GB); John Bishop, Chepstow (GB); Richard Craven, Chepstow (GB)

(73) Assignee: CREO MEDICAL LIMITED, Chepstow (GB)

( * ) Notice: Subject to any disclaimer, the term of this patent is extended or adjusted under 35 U.S.C. 154(b) by 936 days.

(21) Appl. No.: 16/965,245

(22) PCT Filed: Mar. 8, 2019

(86) PCT No.: PCT/EP2019/055911
§ 371 (c)(1),
(2) Date: Jul. 27, 2020

(87) PCT Pub. No.: WO2019/175063
PCT Pub. Date: Sep. 19, 2019

(65) Prior Publication Data
US 2021/0060193 A1    Mar. 4, 2021

(30) Foreign Application Priority Data
Mar. 16, 2018 (GB) ...................................... 1804265

(51) Int. Cl.
*A61L 2/14* (2006.01)
*A61B 90/70* (2016.01)
(Continued)

(52) U.S. Cl.
CPC ................ *A61L 2/14* (2013.01); *A61B 90/70* (2016.02); *A61L 2/0047* (2013.01);
(Continued)

(58) Field of Classification Search
CPC ........ A61L 2/14; A61L 2/0047; A61L 2/0064; A61L 2/26; A61L 2202/24; A61B 90/70;
(Continued)

(56) References Cited

U.S. PATENT DOCUMENTS

| 4,288,882 A | 9/1981 | Takeuchi |
| 5,090,433 A | 2/1992 | Kamaga |

(Continued)

FOREIGN PATENT DOCUMENTS

| CN | 107695051 A | 2/2018 |
| GB | 2520197 A | 5/2015 |

(Continued)

OTHER PUBLICATIONS

Notification of Transmittal of the International Preliminary Report on Patentability issued from the International Preliminary Examining Authority International Application No. PCT/EP2019/055911, dated Jun. 19, 2020.

(Continued)

*Primary Examiner* — Christine T Mui
(74) *Attorney, Agent, or Firm* — ArentFox Schiff LLP

(57) ABSTRACT

The disclosure relates to a sterilization apparatus which uses thermal or non-thermal plasma to disinfect surgical scoping devices such as endoscopes, gastroscopes, laparoscopes and the like. Aspect of the disclosure provide: (i) an apparatus for sterilizing inside an instrument channel formed with an insertion tube of a surgical scoping device, (ii) a whole-device sterilization apparatus for treating the entire exterior surface of a surgical scoping device, and (iii) an apparatus (Continued)

for cleaning and sterilizing a distal end face of an insertion tube of a surgical scoping device.

13 Claims, 8 Drawing Sheets

(51) Int. Cl.
*A61L 2/00* (2006.01)
*A61L 2/26* (2006.01)
*B08B 1/00* (2006.01)
*B08B 7/02* (2006.01)
*B08B 9/02* (2006.01)

(52) U.S. Cl.
CPC .............. *A61L 2/0064* (2013.01); *A61L 2/26* (2013.01); *B08B 1/002* (2013.01); *B08B 7/028* (2013.01); *B08B 9/02* (2013.01); *A61B 2090/701* (2016.02); *A61L 2202/24* (2013.01)

(58) Field of Classification Search
CPC ... A61B 2090/701; B08B 1/002; B08B 7/028; B08B 9/02
USPC ......................................................... 422/186
See application file for complete search history.

(56) References Cited

U.S. PATENT DOCUMENTS

| | | | |
|---|---|---|---|
| 6,936,151 B1* | 8/2005 | Lock ..................... | B03C 5/028 |
| | | | 204/547 |
| 9,248,207 B1 | 2/2016 | Heyoung | |
| 9,522,202 B1 | 12/2016 | Ahiska et al. | |
| 2007/0290620 A1 | 12/2007 | Lee et al. | |
| 2010/0247403 A1* | 9/2010 | Hancock ................... | A61L 2/14 |
| | | | 422/186.29 |
| 2011/0079582 A1 | 4/2011 | Yonesu et al. | |
| 2015/0056107 A1 | 2/2015 | Hancock | |
| 2016/0113700 A1 | 4/2016 | Hancock et al. | |
| 2016/0128769 A1 | 5/2016 | Rontal et al. | |
| 2017/0023122 A1 | 1/2017 | Cordingley | |
| 2017/0232122 A1 | 8/2017 | Hancock | |

FOREIGN PATENT DOCUMENTS

| | | | |
|---|---|---|---|
| GB | 2521611 A | 7/2015 | |
| GB | 2562110 A | 11/2018 | |
| JP | 7-111980 A | 5/1995 | |
| JP | 9-98947 A | 4/1997 | |
| JP | 2003-210556 A | 7/2003 | |
| KR | 10-2008-0101413 A | 11/2008 | |
| RU | 2 367 473 C2 | 9/2009 | |
| WO | WO 00/53341 A1 | 9/2000 | |
| WO | WO 2016/145375 A1 | 9/2016 | |
| WO | WO2018/202759 A2 | 11/2018 | |

OTHER PUBLICATIONS

Notification of Transmittal of the International Search Report and Written Opinion, issued by International Searching Authority in corresponding International Application No. PCT/EP2019/055911, dated Aug. 5, 2019.

Search Report relating to claims 18-28 under Section 17(6), issued by the United Kingdom Intellectual Property Office in counterpart United Kingdom Application No. GB1804265.5, dated Sep. 20, 2019.

Search Report relating to claims 29-32 under Section 17(6), issued by the United Kingdom Intellectual Property Office in counterpart United Kingdom Application No. GB1804265.5, dated Sep. 20, 2019.

Search Report under Section 17(5), issued by the United Kingdom Intellectual Property Office in counterpart United Kingdom Application No. GB1804265.5, dated Feb. 1, 2019.

Written Opinion of the International Preliminary Examining Authority issued from the International Preliminary Examining Authority International Application No. PCT/EP2019/055911, dated Feb. 17, 2020.

* cited by examiner

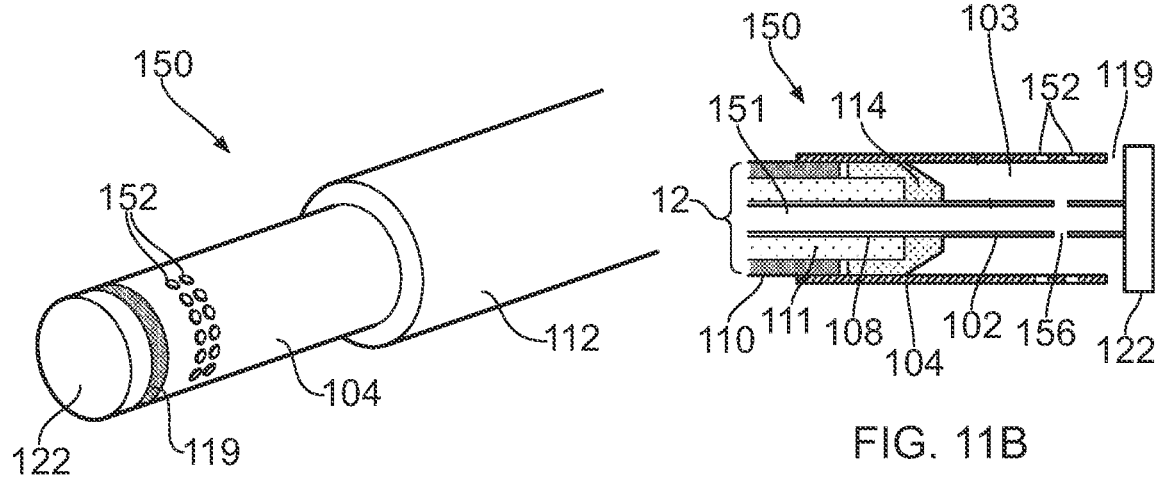
FIG. 11A
FIG. 11B
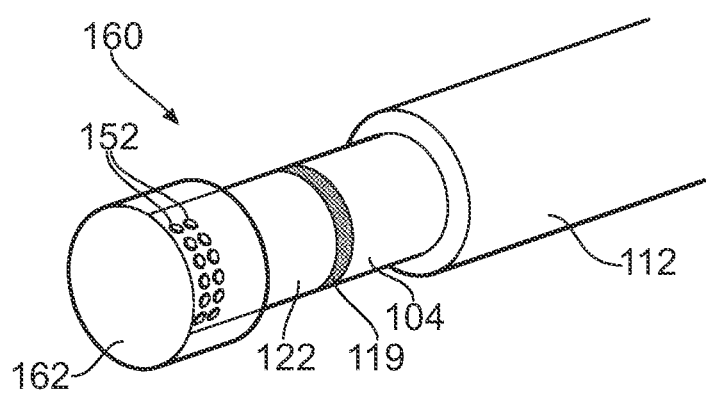
FIG. 12
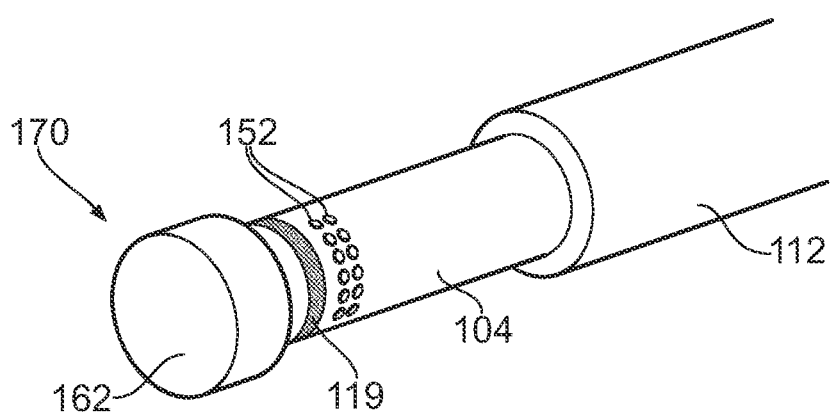
FIG. 13

STERILIZATION APPARATUS

CROSS-REFERENCE TO RELATED APPLICATIONS

This application is a National Stage entry of International Application No. PCT/EP2019/055911, filed on Mar. 8, 2019, which claims priority to British Patent Application No. 1804265.5, filed on Mar. 16, 2018. The disclosures of the priority applications are hereby incorporated in their entirety by reference.

FIELD OF THE INVENTION

The present invention relates to sterilization of surgical scoping devices such as endoscopes, gastroscopes, laparoscopes and the like. In particular, the invention relates to apparatus for sterilizing or disinfecting the instrument channels and/or bodies of such surgical scoping devices.

BACKGROUND TO THE INVENTION

Bacteria are single-celled organisms that are found almost everywhere, exist in large numbers and are capable of dividing and multiplying rapidly. Most bacteria are harmless, but there are three harmful groups; namely: cocci, spirilla, and bacilla. The cocci bacteria are round cells, the spirilla bacteria are coil-shaped cells, and the bacilli bacteria are rod-shaped. The harmful bacteria cause diseases such as tetanus and typhoid.

Viruses can only live and multiply by taking over other cells, i.e. they cannot survive on their own. Viruses cause diseases such as colds, flu, mumps and AIDS. Fungal spores and tiny organisms called protozoa can cause illness.

Such micro-organisms are known to persist in the instrument channel of surgical scoping devices (such as endoscopes, gastroscopes, etc.). It is highly desirable to remove these organisms in order that the surgical scoping devices do not become a source of infection. Sterilization is an act or process that destroys or eliminates all form of life, especially micro-organisms.

Known methods of sterilizing the instrument channels of scopes involve the use cleaning fluids which are flushed through the channel to expel debris. A brush may also be used to scrub the interior. The scope is then disinfected in automatic washing or disinfection units, which may involve the immersion of the scope in potentially harmful chemicals such as glutaraldehyde. Finally, the scope is rinsed thoroughly with water, then alcohol, to remove traces of the disinfectant.

Such known methods are labour-intensive, and are also prone to incomplete or insufficient sterilization of the instrument channel.

SUMMARY OF THE INVENTION

At its most general, the present invention provides sterilization apparatus which uses thermal or non-thermal plasma to disinfect surgical scoping devices such as endoscopes, gastroscopes, laparoscopes and the like. In various aspects, the present invention provides (i) an apparatus for sterilizing inside a channel (e.g. instrument channel) formed with an insertion tube of a surgical scoping device, (ii) a whole-device sterilization apparatus for treating the entire exterior surface of a surgical scoping device, and (iii) an apparatus for cleaning and sterilizing a distal end face of an insertion tube of a surgical scoping device.

In a first aspect, there is provided an apparatus for sterilizing a surgical scoping device, the apparatus comprising: a sterilization instrument insertable through a longitudinal channel that extends along an insertion tube of a surgical scoping device, the sterilization instrument comprising: an elongate probe comprising a coaxial cable for conveying radiofrequency (RF) electromagnetic (EM) energy and/or microwave EM energy, a probe tip connected at the distal end of the coaxial cable for receiving the RF and/or microwave energy, and a gas conduit for conveying gas to the probe tip; wherein the coaxial cable comprises an inner conductor, an outer conductor and a dielectric material separating the inner conductor from the outer conductor, wherein the probe tip comprises a first electrode connected to the inner conductor of the coaxial cable, and a second electrode connected to the outer conductor of the coaxial cable, wherein the second electrode encloses an internal volume of the probe tip, wherein the first electrode extends longitudinally within the internal volume, wherein the probe tip further comprises an insulating cap mounted at a distal end of the coaxial cable to isolate the coaxial cable from the internal volume, wherein the gas conduit is in fluid communication with the internal volume via a flow path formed between the insulating cap and the second electrode, wherein the first electrode and second electrode are configured to receive the RF and/or microwave energy from the coaxial cable to set up an electric field in the internal volume for striking a plasma therein, and wherein the probe tip includes an outlet for releasing plasma from the internal volume.

The apparatus of this aspect thereby allows sterilization of the instrument channel of a scoping device using a thermal and/or non-thermal plasma, which may be particularly effective to destroy bacteria and viruses present on the wall of the instrument channel. The apparatus may be dimensioned to fit instrument channels of conventional scoping devices, but it is also envisaged that the apparatus of the present invention may also be used to sterilize any channel through the insertion tube of a scoping device, such as a biopsy channel. In this respect, it is understood that instrument channel when used in the present specification may be considered to refer to any channel through the insertion cord of a scoping device.

The insulating cap may be mounted within the second electrode, e.g. to define a proximal end of the internal volume. The flow path may comprise a plurality of openings in the second electrode that permit gas flow around the insulating cap. The plurality of openings may be regularly space to facilitate a uniform flow of gas into the internal volume.

The insulating cap may help to ensure that plasma is generated in a distal part of the probe tip, and may also help to direct generated plasma out of the probe tip. In some embodiments, the insulating cap may have a chamfered distal end in the region of an opening through the second electrode. This may help to increase velocity of gas along the flow path the second electrode, aiding throughput of gas and direction of plasma out of the distal end of the probe tip.

The second electrode may be a cylinder. The plurality of openings may each comprise a longitudinal notch in the cylinder. For example, a proximal end of the second electrode may be castellated to provide the plurality of openings.

The apparatus may be configured to generate and deliver hydroxyl radicals for sterilization or disinfection. The apparatus may thus comprise a liquid conduit for delivering water to the internal volume. The liquid conduit may be a hollow passage through the inner conductor of the coaxial cable. In this way, the provision of a further conduit need not require more room in the elongate probe.

The liquid conduit may be configured to deliver water mist into the internal volume. Using water mist or vapour may facilitate generation of hydroxyl radicals from positive ions in the plasma.

The elongate probe may comprise a protective sleeve that defines a lumen through which the coaxial cable extends. The gas conduit may be a passageway formed between an outer surface of the coaxial cable and an inner surface of the protective sleeve. This can also ensure that the apparatus is compact for easy insertion through an instrument channel.

The probe tip may comprise a conductive cap mounted on the first electrode at a distal end of the internal volume. The conductive cap is isolated from the second conductor. For example, the conductive cap may be spaced from a distal end of the second electrode to define the outlet. The conductive cap may ensure that plasma is efficiently produced and helps to direct plasma circumferentially from the end of the probe tip to effectively sterilize the inner wall of the instrument channel. The conductive cap effectively acts as an extension of the first electrode for generation of plasma.

The first electrode may be helical. A helical electrode advantageously provides series resonance in the electrode at the microwave frequency, thereby delivering maximum energy into the gas and plasma. The first electrode is formed from a portion of the inner conductor of the coaxial cable that extends beyond a distal end of the outer conductor.

The apparatus may comprise a withdrawal device mounted on the elongate probe and configured to retract the elongate probe therethrough. The withdrawal device may be configured to withdraw the elongate probe at a predetermined rate. For example, the withdrawal device may comprise a motor drivable to retract the elongate probe. In this way the apparatus may be configured to operate automatically and with no human control. The predetermined rate may be selected to ensure thorough sterilization of the instrument channel. The predetermined rate may be less than 10 mm per second, e.g. 5 mm per second, preferably 1 mm per second or less, such as 0.5 mm per second or less.

The probe tip may further comprise a cleaning brush mounted at a distal end thereof. The cleaning brush may assist in removing or releasing biofilms from the surface of the instrument channel.

The apparatus may comprise a vibration excitation device configured to impart ultrasonic vibrations to the elongate probe or the probe tip or a brush mounted on the probe tip. The vibration excitation device may be a motor (e.g. linear or stepper motor), or an ultrasonic transducer or a piezoelectric actuator. In some embodiments, the vibration excitation device may be or be incorporated into the withdrawal device. In other examples, the vibration excitation device may be an independent device, e.g. mounted on the elongate probe or within the probe tip.

In a second aspect, there is provided an apparatus for sterilizing a surgical scoping device, the apparatus comprising: a housing that defines an enclosure for receiving a surgical scoping device; a plasma applicator mounted in the housing, the plasma applicator comprising a plasma generating region and an outlet for directing generated plasma out of the plasma generating region into the enclosure; a power generator connected to deliver RF and/or microwave EM energy to the plasma applicator; a gas supply connected to deliver gas to the plasma applicator. With this device, the external surface of an entire surgical scoping device can be sterilized. In one example, the enclosure may be arranged to receive the whole device. The enclosure may be a microwave cavity. For example, it may resemble a microwave oven. In some examples, the apparatus may adapt conventional industrial washing machines, e.g. to provide the plasma applicator around the drum of the washing machine, whereby the drum becomes the enclosure defined above.

The housing may include a turnable for rotating the surgical scoping device within the enclosure.

The apparatus in this aspect may also make use of hydroxyl radicals for sterilization. For example, the apparatus may comprise a liquid supply for delivering water into the enclosure. The liquid supply may be via a conduit having a nozzle arranged to deliver water mist into the enclosure. In other examples the water may be supplied into the plasma generating region of the plasma applicator.

The instrument channel of the scoping device may simultaneously be sterilized by an apparatus according to the first aspect of the invention, as defined above. Optionally, the apparatus may comprise more than one such devices, whereby multiple channels within the insertion tube of the scoping device may be sterilized simultaneously.

The housing may comprise a panel that defines a surface of the enclosure, wherein the panel has an array of plasma applicators mounted therein. For example, a top wall or sidewall of the enclosure may comprise an array of plasma applicators. In this way, it can be ensured that plasma is directed at all outer surfaces of the scoping device, and that the scoping device is thoroughly sterilized.

The enclosure may comprise a body portion for receiving a body of the surgical scoping device, and an annular region for receiving an insertion tube of the surgical scoping device. The annular region may comprise an annular plasma generator configured to move relative to the insertion tube of the surgical scoping device. For example, the annular plasma generator may be mounted on a treatment bed that is movable relative to the body portion along the length of the insertion tube of the surgical scoping device.

In some embodiments, the treatment bed may be movable so as to move the annular plasma generator relative to the insertion tube. The plasma applicator may be moved by movement of the treatment bed to ensure that the entire outer surface of the insertion tube is properly sterilized by plasma produced by the annular plasma generator. In some embodiments, the treatment bed may be a conveyor belt so that the apparatus may be compact.

According to a third aspect of the invention, there is provided an apparatus for sterilizing a surgical scoping device, the apparatus comprising: a housing that defines a recess for receiving a distal end of an insertion tube of a surgical scoping device; a brush mounted in the recess to contact the distal end of the insertion tube; a drive element operably connected to the brush to cause relative motion of the brush within the housing. This apparatus is primarily for physically cleaning the distal end face of the insertion tube. However, the apparatus may further comprise a plasma applicator mounted in the housing, the plasma applicator comprising a plasma generating region and an outlet for directing generated plasma out of the plasma generating region into the recess. The apparatus may thus both clean and sterilise the distal end face.

The housing may be connected to a power generator arranged to deliver RF and/or microwave EM energy to the plasma applicator, and to a gas supply arranged to deliver gas to the plasma applicator. The housing may further may connected to a liquid supply for delivering water into the recess, whereby hydroxyl radicals can be generated to assist with sterilization and disinfection.

The term "surgical scoping device" may be used herein to mean any surgical device provided with an insertion tube that is a rigid or flexible (e.g. steerable) conduit that is introduced into a patient's body during an invasive procedure. The insertion tube may include the instrument channel and an optical channel (e.g. for transmitting light to illuminate and/or capture images of a treatment site at the distal end of the insertion tube. The instrument channel may have a diameter suitable for receiving invasive surgical tools. The diameter of the instrument channel may be 5 mm or less.

Herein, the term "inner" means radially closer to the centre (e.g. axis) of the instrument channel and/or coaxial cable. The term "outer" means radially further from the centre (axis) of the instrument channel and/or coaxial cable.

The term "conductive" is used herein to mean electrically conductive, unless the context dictates otherwise.

Herein, the terms "proximal" and "distal" refer to the ends of the elongate probe. In use the proximal end is closer to a generator for providing the RF and/or microwave energy, whereas the distal end is further from the generator.

In this specification "microwave" may be used broadly to indicate a frequency range of 400 MHz to 100 GHz, but preferably the range 1 GHz to 60 GHz. Specific frequencies that have been considered are: 915 MHz, 2.45 GHz, 3.3 GHz, 5.8 GHz, 10 GHz, 14.5 GHz and 24 GHz. In contrast, this specification uses "radiofrequency" or "RF" to indicate a frequency range that is at least three orders of magnitude lower, e.g. up to 300 MHz, preferably 10 kHz to 1 MHz, and most preferably 400 kHz. The microwave frequency may be adjusted to enable the microwave energy delivered to be optimised. For example, a probe tip may be designed to operate at a certain frequency (e.g. 900 MHz), but in use the most efficient frequency may be different (e.g. 866 MHz).

BRIEF DESCRIPTION OF THE DRAWINGS

Embodiments of the invention will now be described by way of example with reference to the accompanying drawings, in which:

FIG. 11A is a schematic perspective view of a probe tip for generating hydroxyl radicals that can be used with the invention;

FIG. 11B is a cross-sectional view through the probe tip of FIG. 11A;

FIG. 12 is a schematic perspective view of another probe tip for generating hydroxyl radicals that can be used with the invention;

FIG. 13 is a schematic perspective view of yet another probe tip for generating hydroxyl radicals that can be used with the invention.

DETAILED DESCRIPTION; FURTHER OPTIONS AND PREFERENCES

Figure 1:
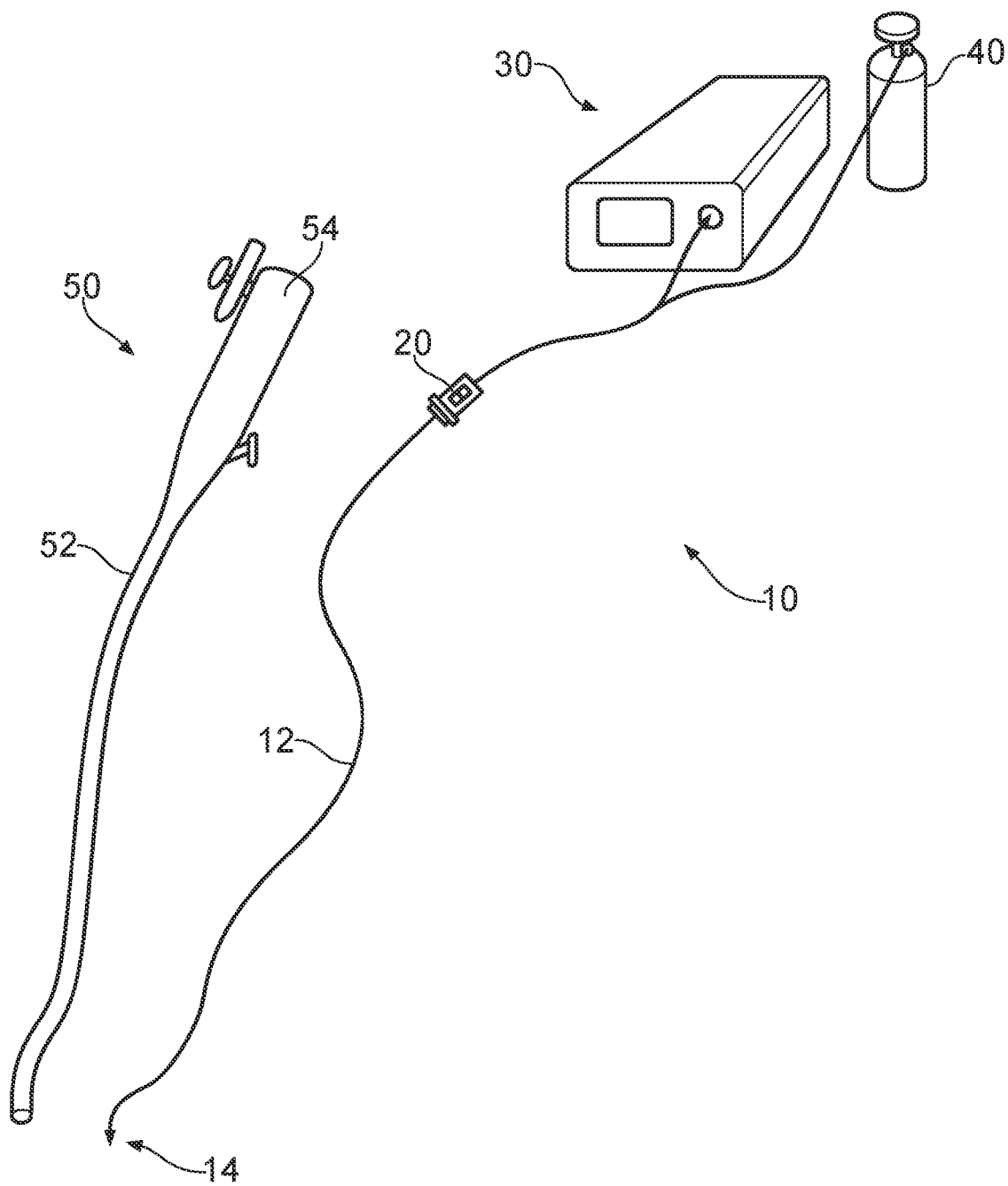
FIG. 1 shows a sterilization apparatus that is an embodiment of the invention.

FIG. 1 shows a sterilization apparatus 10 that is an embodiment of the invention. The sterilization apparatus comprises an elongate probe, e.g. having the form of a flexible shaft. The elongate probe comprises a coaxial cable 12 having a probe tip 14 at its distal end. The elongate probe may include a protective sleeve in which the coaxial cable 12 is conveyed, but this is not essential. A generator 30 is connected to a proximal end of the coaxial cable 12. A gas supply 40 is also connected to the elongate probe to supply gas to the probe tip 14 through a gas conduit (not shown) that extends through the elongate probe. The gas conduit may form part of the coaxial cable 12, e.g. may be a longitudinal hollow passageway formed within the coaxial cable, e.g. within its inner conductor. Alternatively, the gas conduit may be a separate tube or passageway extending alongside the coaxial cable, e.g. within the protective sleeve. The gas supply 40 may be a supply of any suitably inert gas for formation of a non-thermal or thermal plasma, e.g. argon, helium, nitrogen, carbon dioxide or a combination thereof. In some examples, it may also be desirable to supply ultraviolet (UV) light to assist in the sterilization process.

The elongate probe is configured, e.g. dimensioned, to fit within one or more channels that extends along the length of an insertion tube 52 of a surgical scoping device 50, such as an endoscope, gastroscope, bronchoscope or the like. In the discussion below, the elongate probe is insertable into the instrument channel of the insertion tube. However, the present invention may be applicable to the sterilization of any channel through the insertion tube, e.g. an exhaust channel for flushing debris away from a treatment site during normal use.

The apparatus 10 further comprises a withdrawal device 20 that is arranged to move longitudinally the elongate probe so as to enable controllable withdrawal in the instrument channel, as explained in more detail below. The withdrawal device 20 may be configured to run in both a forward and a reverse direction, such that the withdrawal device 20 may be used both to insert and to withdraw the elongate probe through the instrument channel.

The coaxial cable 12 and probe tip 14 are insertable through an instrument channel of an insertion tube 52 of a scoping device 50. The elongate probe may be inserted manually by a user, or may be inserted using the withdrawal device 20. The instrument channel may be flushed with a liquid prior to insertion of the elongate probe, in which case the sterilization apparatus 10 may be used to dry the instrument channel as it is inserted, and to sterilize or disinfect the instrument channel while the probe tip 14 is withdrawn through the instrument channel. The elongate probe itself may be used to introduce a liquid, e.g. through the gas conduit or a separate liquid-conveying conduit, as it is inserted into or withdrawn from the instrument channel.

The apparatus 10 functions to sterilize an interior of the instrument channel as it is withdrawn therefrom. It may be used in conjunction with an apparatus for sterilizing an exterior of the scoping device 50, e.g. its body 54 and/or insertion tube 52.

In operation, during withdrawal of the probe tip 14 through the instrument channel, the generator 30 supplies radiofrequency (RF) electromagnetic (EM) energy and/or microwave EM energy to the probe tip 14. The gas supply 40 simultaneously supplies gas to the probe tip 14 via the gas conduit. The RF and/or microwave energy and supplied gas are combined at the probe tip to generate a thermal or non-thermal plasma, which is emitted from the probe tip 14 to contact an inner surface of the instrument channel to destroy or eliminate micro-organisms. Examples of plasma generation in this manner are disclosed in WO 2009/060213 A1, for example.

The generator may be controlled to determine whether the generated plasma is a non-thermal or thermal plasma. For example, the supply microwave energy may have a power and/or duty cycle that is selectable to produce non-thermal or thermal plasma. In some examples, thermal plasma may be used to dry out the interior of the instrument channel following sterilisation. This may be advantageous as it obviates the need to hang the scoping device for drying after cleaning and speeds up the whole scope processing cycle.

The withdrawal device 20 may be arranged to control the withdrawal rate of the probe tip. The withdrawal rate may be slow, e.g. less then 10 mm per second, preferably less than 1 mm per second, such as 0.5 mm per second. The withdrawal rate may be constant. Using a mechanical withdrawal device enables better control over such slow withdrawal rates than can be achieved manually.

In some examples, it may be desirable for water (e.g. water mist or vapour) to be present at the distal end of the elongate probe when the plasma is generated. In this scenario, the plasma may generate hydroxyl radicals from the water. The hydroxyl radicals are effective sterilizing agents. The water may be supplied through the elongate probe. In one example, the water is supplied through an longitudinal passageway formed within the inner conductor of the coaxial cable. Meanwhile the gas conduit may be an annular space formed between an outer surface of the outer conductor of the coaxial cable and an inner surface of a protective sleeve. In this way, both gas and liquid can be delivered to the plasma generation region, thereby permitted localised generation of hydroxyl radicals. In some embodiments, the apparatus may be configured to receive ultraviolet radiation to facilitate formation of the hydroxyl radicals. Examples of hydroxyl radical generation in this manner are disclosed in WO 2009/060214 A1, for example.

The apparatus 10 may further comprise a vibration excitation device configured to cause relative vibration between the insertion tube and the elongate probe. The vibration excitation device may be integrated with the withdrawal device 20, e.g. as an alternative operational modality. In a vibration operating mode, the withdrawal device 20 may be arranged to cause rapid (e.g. ultrasonic) small-amplitude oscillation of the elongate probe within the instrument channel. In other examples, the vibration excitation device may operate independently of the withdrawal device. For example, the vibration excitation device may comprise a suitable motor (e.g. stepper or linear motor) or a piezoelectric element configured to cause relative ultrasonic vibration between the elongate probe and insertion tube. The vibration excitation device may be mounted on either the elongate probe or the insertion tube. The purpose of the vibration is to assist or facilitate removal of bio-film or other detritus from the instrument channel.

The vibration excitation device may be connected at a proximal end of the elongate probe, i.e. in close proximity to the withdrawal device 20. Alternatively or additionally, the vibration excitation device may be located at a proximal end of the elongate probe, e.g. at or on the probe tip. The vibration excitation device may be arranged to vibrate the probe tip itself, or a brush mounted on the probe tip. In this example, the vibration excitation device may comprise a piezoelectric element or miniature motor connected to or near the brush or the plasma applicator. The frequency vibrations excited by the vibration excitation device may be in the range 20 kHz to 10 MHz.

Figure 2:
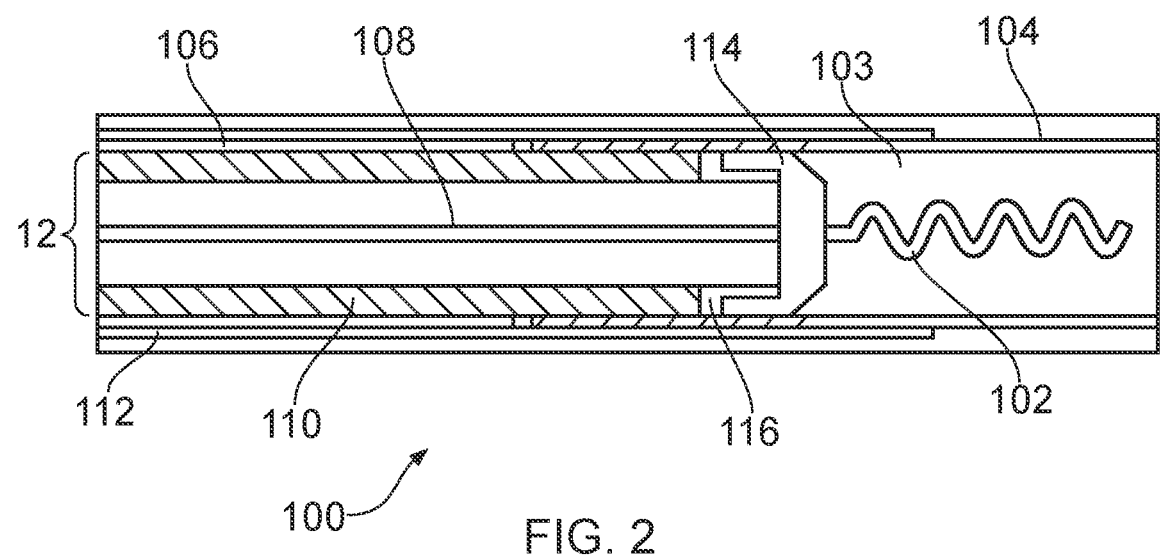
FIG. 2 shows a cross-section view of a first probe tip for use with the present invention.

FIG. 2 shows a cross section view of a first probe tip 100 for use in the present invention, e.g. for using in the apparatus 10 discussed above. Probe tip 100 can be connected to the distal end of a coaxial cable 12 as shown in FIG. 1. The probe tip 100 is configured to receive RF and/or microwave EM energy and gas in order to produce a thermal or non-thermal plasma which can be directed out of the distal end of the probe tip 100 to be directed at the wall of the instrument channel for sterilization as the probe tip 100 is withdrawn from the instrument channel of the scoping device 50.

In this embodiment, the probe tip 100 comprises a first electrode 102 and a second electrode 104 at a distal end thereof. The first electrode 102 has a helical shape and the second electrode 104 is a hollow cylinder which is open at each end, wherein the first electrode 102 is positioned generally along the longitudinal axis of the second electrode 104. A space 103 (also referred to as a plasma generating region) is thereby defined between the first electrode 102 and the second electrode 104.

Figure 3:
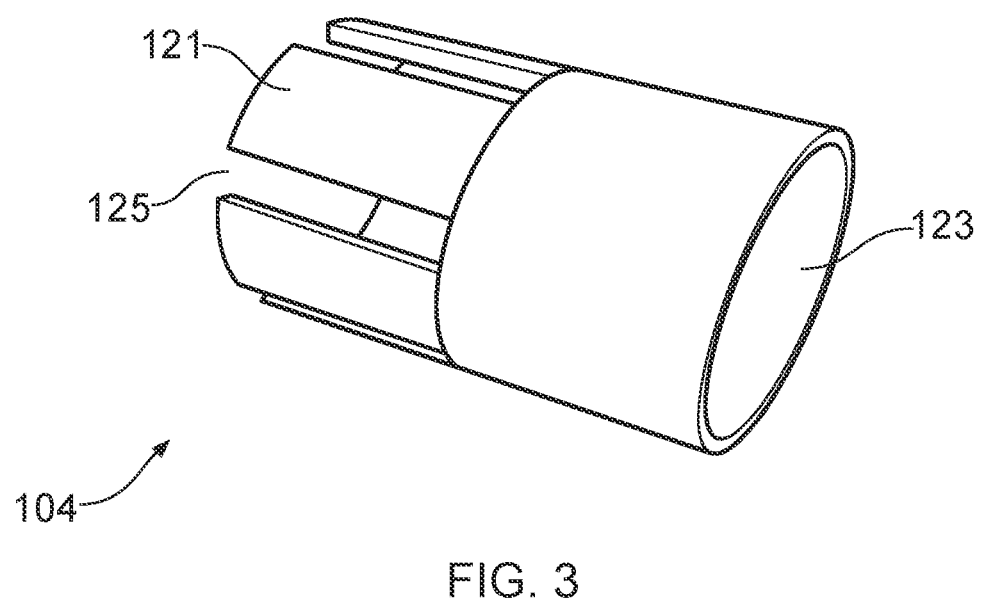
FIG. 3 is a perspective view of a second electrode which is used with the first probe tip.

The second electrode 104 has castellations (i.e. a series protruding fingers 121 separated by notches 125 as shown in FIG. 3) formed in a proximal end. The castellations permit gas to flow from an annular gas conduit 106 surrounding coaxial cable 12 into the space within the second electrode 104. A plasma may be struck by configuring the supplied RF and/or microwave EM radiation to generate a high electric field between the first electrode 102 and the second electrode 104 in the space 103. The plasma may be struck using RF EM energy, and sustained by the microwave EM energy. The generated plasma flows out of the distal open end of the second electrode 104 to contact the inner surface of the instrument channel in which the elongate probe is inserted.

The coaxial cable 12 comprises an inner conductor 108 separated from an outer conductor 110 by an insulating dielectric material 111. The first electrode 102 is connected to an inner conductor 108 of the coaxial cable and the second electrode 104 is connected to an outer conductor 110 of the coaxial cable 12. In some embodiments, the first electrode 102 may additionally comprise a cap at its distal end, such as a cap 218 shown in FIG. 4 and discussed below.

The gas conduit 106 may be formed by an annular gap between an outer surface of the outer conductor 110 of the coaxial cable and a protective sleeve 112 which surrounds the coaxial cable 12. As discussed above, gas can be introduced to the gas conduit 106 at or around the proximal end of the coaxial cable 12 from a gas supply 40.

The second electrode 104 is configured to fit over the outer conductor 110 and within the sleeve 112 at the distal end of the coaxial cable 12. The second electrode 104 therefore sits within the gas conduit 106 at its distal end. Gas is able to flow from the gas conduit 106 to within the second electrode 104 through the castellations which are formed in the proximal end of the second electrode 104.

Within the second electrode 104, positioned at the distal end of the coaxial cable 12, is a generally cylindrical ceramic cap 114. The ceramic cap 114 is spaced away from a distal end of the outer conductor 110 of the coaxial cable 12. A longitudinal gap 116 between these parts may be filled with an adhesive, e.g. a UV-curing adhesive, to prevent any arcing between the outer conductor 110 and the inner conductor 108.

The ceramic cap 114 may extend for around 2 mm in the longitudinal direction. The ceramic cap 114 has a chamfered distal end face to encourage gas flowing from the gas conduit 106 into the space 103 to pass between the first electrode 102 and second electrode 104, where the plasma is struck. The first electrode 102 is connected to the inner conductor 108 of the coaxial cable by a conductive element (not shown) that extends through the ceramic cap 114. The conductive element may be a portion of the inner conductor 108 that protrudes beyond the distal end of the outer conductor 110.

The first electrode 102 of this embodiment is formed from a wire which is twisted to form a helical or spiral structure. The wire in some embodiments may be wound around a solid core of a dielectric material, e.g. PTFE, PEEK or a ceramic material. Alternatively, the wire may be wound around a thin-walled open cylinder. The wire may preferably made from a good conductor such as copper, silver, gold or plated steel to ensure that conductor losses are minimised in the probe tip 100. The wire may be a distal portion of the inner conductor 108 that extends out of a distal end of the coaxial cable 12.

The first electrode 102 is configured to be a resonant structure at the microwave frequencies used with the present invention. At these frequencies, the wire forming the first electrode 102 displays inductive behaviour. By forming the first electrode 102 as a helix, there is a capacitance created between each adjacent turn when energy is supplied to the tip 100. This structure therefore creates appropriate conditions for series resonance in the first electrode 102, having a minimum impedance at the microwave frequency of EM energy supplied to the probe tip 100.

FIG. 3 shows a perspective view of an example of the second electrode 104. The second electrode 104 is a hollow cylinder having an open distal end 123 to allow plasma produced within the electrode to flow out of the distal end. The proximal end of the electrode 104 is also open, such that the electrode can be fitted to the distal end of a coaxial cable in a manner as described above. The proximal end of the electrode 104 is castellated such that a plurality of notches 125 are formed between fingers 121 in the proximal end of the electrode 104. These notches 125 allow gas to flow to the interior of the electrode 104 from a gas conduit 106, as described above, where the gas is struck to create a thermal or non-thermal plasma. It may be desirable to have a plurality of notches spaced regularly around the circumference of the second electrode 104 so that the flow of gas into the space 103 is substantially uniform relative around the longitudinal axis.

The second electrode 104 has a total length of at least 11 mm, where the distance between the base of the castellations and the distal end of the second electrode 104 is at least 3 mm, preferably at least 5 mm. For example, the distance may be 6.8 mm. This distance is generally equivalent to the length of the volume within the second electrode 104 in which the thermal or non-thermal plasma is generated.

Figure 4:
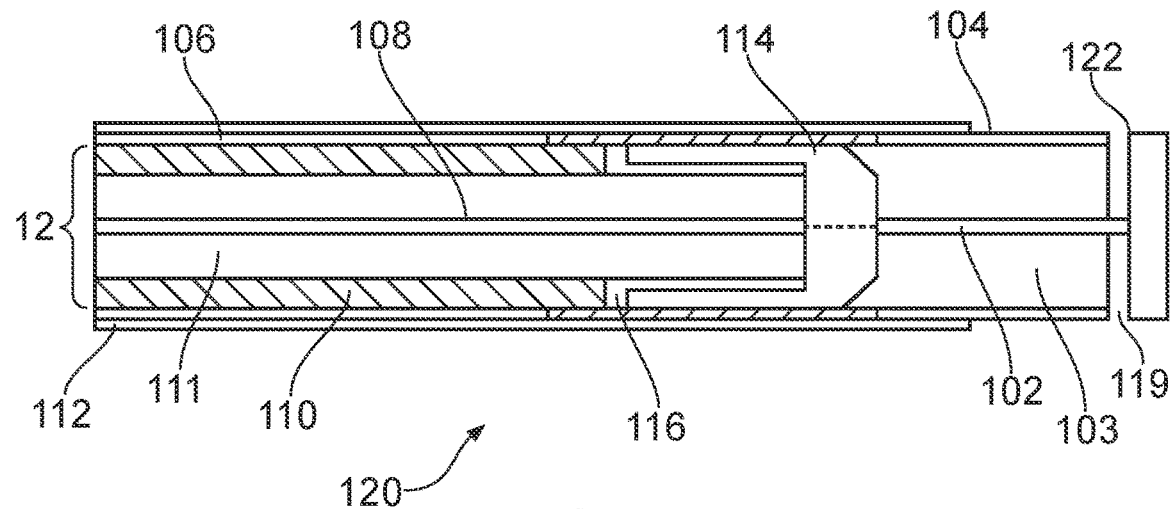
FIG. 4 shows a cross-section view of a second probe tip for use with the present invention.

FIG. 4 shows a cross section view of a second embodiment of a probe tip 120 for use with the present invention. Features of the second probe tip 120 which correspond with the first probe tip 100 have been given the same reference numerals, and are not described again. The probe tip 120 is fitted at the distal end of a coaxial cable in a similar manner as the first probe tip 100 described above.

In the probe tip 120, the first electrode 102 is straight rather than helical. For example, the first electrode 102 may simply be an extension of the inner conductor 108 of the coaxial cable. At the distal end of the first electrode 102 is a conductive end cap 122, which is spaced away from the distal end of the second electrode 104 to define a gap 119. The probe tip 120 is configured to receive RF and/or microwave EM energy and gas in order to produce a thermal or non-thermal plasma. The probe tip 120 operates in a similar manner as probe tip 100 described above.

The end cap 122 assists in maintaining the thermal or non-thermal plasma and also operates to direct the plasma towards the wall of the instrument channel for sterilization as the probe tip 120 is withdrawn from the instrument channel of the scoping device 50. The end cap 122 may be a circular disc, e.g. having a diameter similar to (preferably slightly greater than) an outer diameter of the second electrode 104. The end cap 122 is made of a conductive material such as copper, silver, gold or plated steel. The end cap 122 is connected to the distal end of the first electrode 102 such that there is a gap of around 0.5 mm between the distal end of the second electrode 104 and the end cap 122. An end cap may also be used in embodiments having a helical first electrode, such as probe tip 100 shown in FIG. 2.

Figure 5:
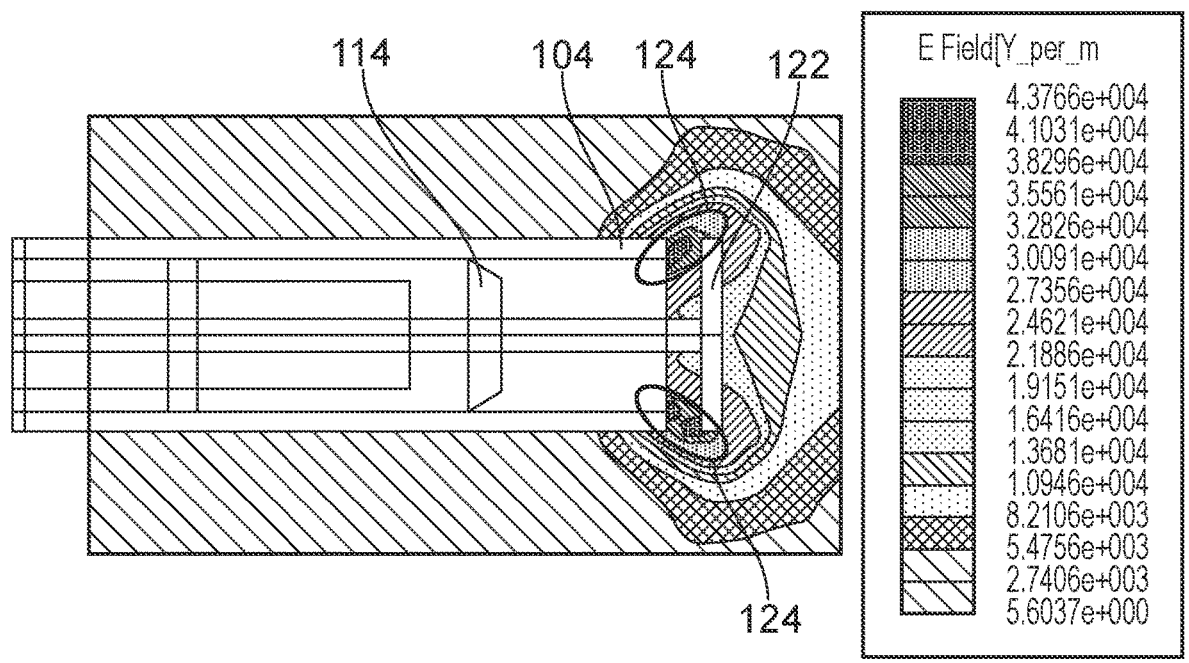
FIG. 5 is a computer-simulated model showing the location of plasma generated by the second probe tip.

FIG. 5 is a computer-generated simulation showing electric field strength around the probe tip 120 when in use. It can be seen that the presence of the end cap 122 acts to concentrate the electric field in an annular region 124 that extends between a distal end of the second electrode 104 and a longitudinally opposed portion of the end cap 122. This indicates that plasma can be generated in this region, whereupon the flow of gas through the space 103 will be deflected by the end cap 122 to direct the plasma on to the inner surface of the instrument channel.

Although not shown in FIG. 2 or 4, the probe tip may further comprise a brush e.g. mounted beyond the distal end of the second conductor. The brush may comprises a plurality of deformable bristles configured to rub against the inner surface of the instrument channel to assist in the sterilization and cleaning process.

Figure 6:
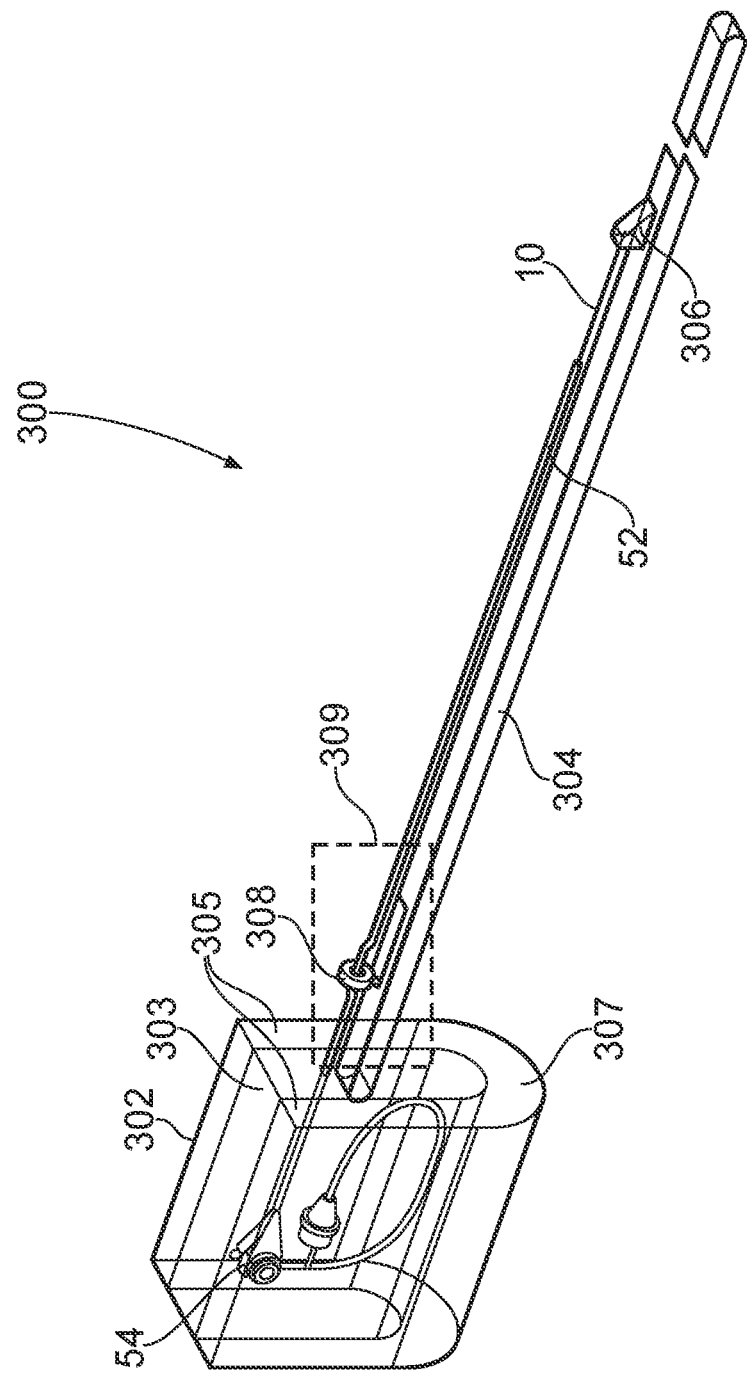
FIG. 6 is a schematic view of a whole surgical scoping device sterilization apparatus that is an embodiment of the invention.

FIG. 6 shows a schematic view of an apparatus 300 for simultaneously sterilizing the body 54 and instrument channel of a scoping device 50. It may be referred to herein as a whole surgical scoping device sterilization apparatus. For clarity, parts of the apparatus are shown to be transparent in FIG. 6. Transparency is not essential to the invention.

The apparatus 300 comprises a head chamber 302 which receives the body 54 of a scoping device. The head chamber 302 is arranged to generate a thermal or non-thermal plasma for cleaning and sterilizing the external surfaces of the body 54. The head chamber 302 comprises an internal volume 303 formed between a housing that defines a U-shaped cross-section. The body 54 is insertable into the volume 303 between a pair of upstanding panels 305 (which form the arms in the U-shaped cross-section).

The volume 303 is a sterilization zone in which plasma and/or hydroxyl radicals are applied to the body 52. The body 54 may be introduced into the volume 303 through an opening in a top surface thereof, e.g. between the panels 305. Alternatively, a base 307 of the head chamber 302 may be detachable from the panels 305 to form an opening into the volume 303. In another example, one or both of the panels may be pivotably connected to the base 307 whereby they can rotate away from their upright position to enable the body 54 to be inserted. Accordingly, the head chamber 302 may be openable for positioning of a body 54 within the chamber, and closable for sterilization. At least one of the upstanding panels 305 of the head chamber 302 may comprise means for holding the body 54 of the scoping device in place within the head chamber 302. For example, the body 54 may be held in place with a hook or hooks.

An array of plasma applicators may be arranged on the inside surface of the panels 305 that face into the volume 303. Each plasma applicator may be arranged to receive a supply of gas (e.g. argon) and RF and/or microwave EM energy from an suitable generator (not shown). Each plasma applicator may have an enclosed plasma generating region and an outlet for directing plasma out of the plasma generating region towards the body 54 of the scoping device. For example, each plasma applicator may comprise a structure corresponding to one of the probe tips described above with respect to FIGS. 2 to 5.

The head chamber 302 may additionally or alternatively be configured to generate hydroxyl radicals (also referred to herein as OH radicals) for sterilization of the body 54 of the scoping device. In general, OH radicals may be generated by supplied water, preferably as a mist or vapour, in the plasma generating region of the plasma applicators discussed above. The generation of a plasma in a region comprising water can cause the formation of hydroxyl radicals, e.g. through reaction with energetic positive ions in the plasma.

Sterilization using OH radicals may be achieved using the plasma applicators described above in conjunction with a separate water inlet (not shown) for introducing water (e.g. water mist) into the volume 303.

Alternatively, the OH radicals may be generated at each plasma applicator, e.g. by arranging for a water supply to be provided to each plasma applicator. The plasma applicators may be adapted so that the plasma is directed into a water mist before being directed into the volume 303, so that the output from each applicator is primarily OH radicals. The head chamber 302 may thus comprise an array of applicators having an OH radical generating region and an outlet for directing generated OH radicals out of the OH radical generating region towards the body 54 of the scoping device. The head chamber 302 may further be configured to confine the OH radicals in the head chamber 302, for example by providing cover elements that can close openings of the volume 303 between the upstanding panels 305 of the head chamber 302, e.g. at the ends and top thereof.

For the generation of OH radicals the head chamber 302 may comprise a mist generator which is connected to deliver water mist (i.e. moisture of fog) into the OH radical generating region of each applicator. Each applicator may also comprise a gas feed connected to deliver gas into the OH radical generating region, the applicator may thereby create a thermal or non-thermal plasma to create an ionisation discharge for generating OH radicals for delivery out of the applicator.

For sterilization of the internal surface of the instrument channel within insertion tube 52, an apparatus 10 as shown in FIG. 1 can be used. In use, the elongate probe can be inserted through the instrument channel from a distal end of the insertion tube 52 towards its proximal end such that in an initial position the probe tip 14, which may be a probe tip as described above with respect to FIGS. 2 to 5, is at a proximal end of the instrument channel, e.g. at or within the body 54 of the scoping device.

The apparatus 300 further comprises a treatment bed 304, which may be configured to move linearly, or may be provided as a conveyor belt as explained below. A proximal end of the elongate probe protrudes from the distal end of the insertion tube 52 and is fixed to the treatment bed 304 at an anchor 306. The elongate probe may be connected to a generator and a gas supply (not shown) via the anchor 306. For example, the generator and gas supply may be connected to the anchor 306, which may include interface ports for communicating with the elongate probe. Alternatively, the elongate probe may extend through the anchor to connect directly with the generator and gas supply.

An annular plasma generator 308 for sterilizing an external surface of the elongate probe is mounted on the treatment bed 304. The annular plasma generator 308 is discussed in more detail below with respect to FIG. 7.

In this example, the insertion tube 52 is not fixed to the treatment bed 304, but is mounted in a fixed position with respect to the head chamber 302 containing the body 54 of the scoping device.

In use, the treatment bed 304 and insertion tube 52 move relative to each other, e.g. by moving the treatment bed 304 in a longitudinal direction away from the head chamber 302. The anchor 306 and the annular plasma generator 308 are fixed to the treatment bed 304, so this relative movement causes the probe tip to be withdrawn through the instrument channel and causes the annular plasma generator 308 to pass over the exterior surface of the insertion tube 52. During this movement, the probe tip 14 and the annular plasma generator 308 are configured to generate a thermal or non-thermal plasma, such that the instrument channel and the outer surface of the insertion tube 52 are sterilized.

The treatment bed 304 may move at a rate of less than 1 mm per second, such as 0.5 mm per second. Motion may be continuous or may be in discrete steps, each of less than 1 mm. The apparatus 300 may thereby provide automatic sterilization of an entire scoping device with minimal human intervention.

It may be understood that the relative movement can be achieved in other ways. For example, the head chamber may movement longitudinally with respect to the treatment bed 304. In another example, the annular plasma generator 308 may be movable independently, e.g. to slide with respect to the treatment bed. The exterior of the insertion tube 52 may thus be sterilized separately form the instrument channel.

The treatment bed 304 may be provided in the form of a conveyor belt. This may reduce the length of the apparatus 300 as the anchor point 306 may be mounted to the conveyor belt such that it loops around the end point of the conveyor belt whilst maintaining the direction in which the probe tip 14 and elongate probe are withdrawn through the instrument channel.

Figure 7:
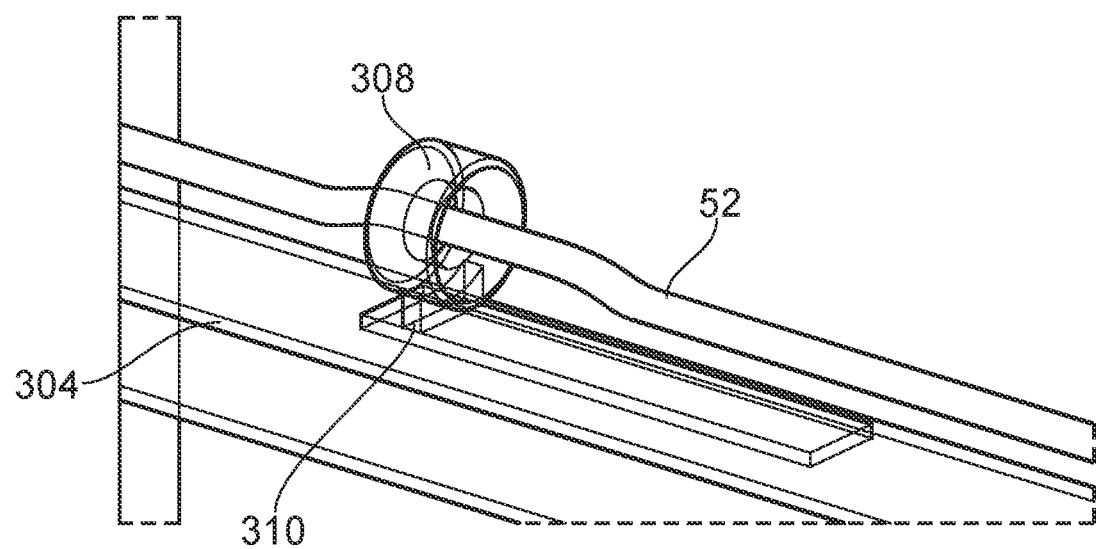
FIG. 7 is a close up view of an annular plasma generator of the sterilization apparatus shown in FIG. 6.

FIG. 7 is an enlarged view of the highlighted area 309 of FIG. 6, in particular showing the annular plasma generator 308. The annular plasma generator 308 is mounted to the treatment bed 304 on a stand 310 such that movement of the treatment bed 304 in a longitudinal direction also moves the annular plasma generator 308. The insertion tube 52 is mounted through the centre of the annular plasma generator 308. Generated plasma is directed towards the surface of the instrument cord 52 around its entire circumference to ensure that the instrument cord 52 is completely sterilized as the annular plasma generator 308 is passed over it by movement of the treatment bed 304.

The annular plasma generator 308 is connected to a gas supply and a generator, e.g. via connections through the stand 310. The generator may supply RF and/or microwave EM energy to enable a plasma to be struck and sustained by one or more plasma applicators mounted in the annular plasma generator 308. The plasma applicators may be oriented in a radial direction so that generated plasma is directed into the circular space surrounded by the annular plasma generator 308. Each plasma applicator may be configured in a similar way to the probe tip 14 discussed above.

The annular plasma generator 308 may be configured in any suitable way to ensure that plasma is generated and directed on to the exterior surface of an elongate probe that passes therethrough.

Figure 8:
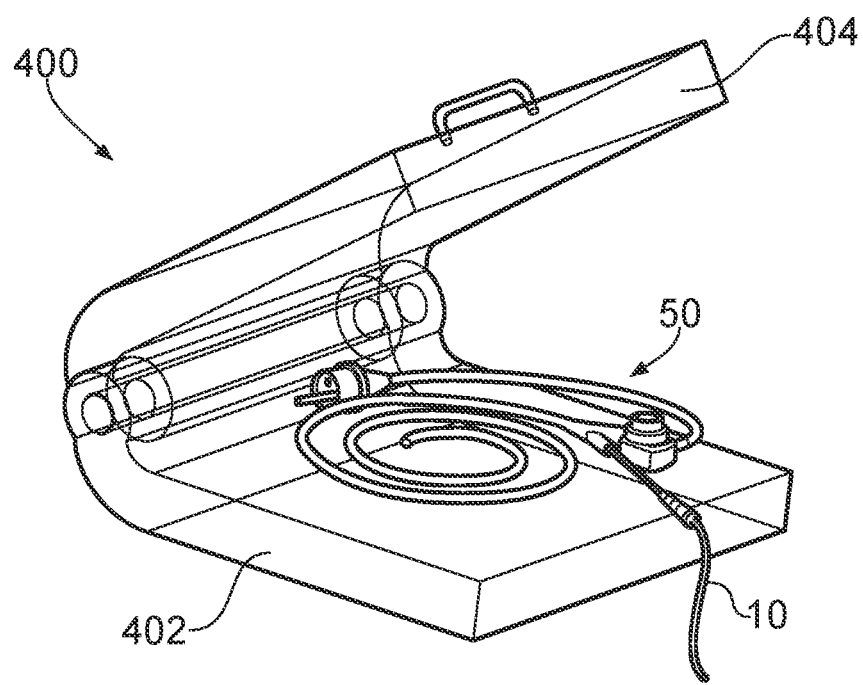
FIG. 8 is a schematic view of a whole surgical scoping device sterilization apparatus that is another embodiment of the invention.

FIG. 8 is a schematic view of a whole surgical scoping device sterilization apparatus 400 that is another embodiment of the invention. The apparatus 400 comprises a base portion 402 and a lid portion 404 which are pivotably connected along one edge. In a closed position, the base portion 402 and lid portion 404 define an internal volume that is configured to receive an entire scoping device 50, i.e. both the body 54 and insertion tube 52. The apparatus 400 may therefore be relatively compact, and in some embodiments may be portable.

In an open position, the base portion 402 and the lid portion 404 are detached to expose the internal volume to receive the scoping device 50.

At least one of the base portion 402 and the lid portion 404 comprises a panel that houses one or more plasma applicators which are arranged to direct generated plasma to the outer surfaces of the scoping device 50. In some embodiments, at least one of the base portion 402 and the lid portion 404 may additionally or alternatively comprise a number of OH radical applicators for sterilization of the scoping device 50, in a similar way to the head chamber 302 of the sterilization apparatus 300 described above with respect to FIG. 6.

While the scoping device 50 is in the volume between the base portion 402 and the lid portion 404, the instrument channel of the scoping device 50 may be sterilized using a sterilization apparatus 10 as shown in FIG. 1.

The internal volume of the apparatus may comprise a microwave cavity into which microwave EM energy is launched. The generator in such an example may comprise a magnetron or a suitable semiconductor amplifier. The apparatus may include a water inlet (not shown) to enable a mist to be produced within the internal volume, whereby OH radicals are generated by the plasma.

Figure 14:
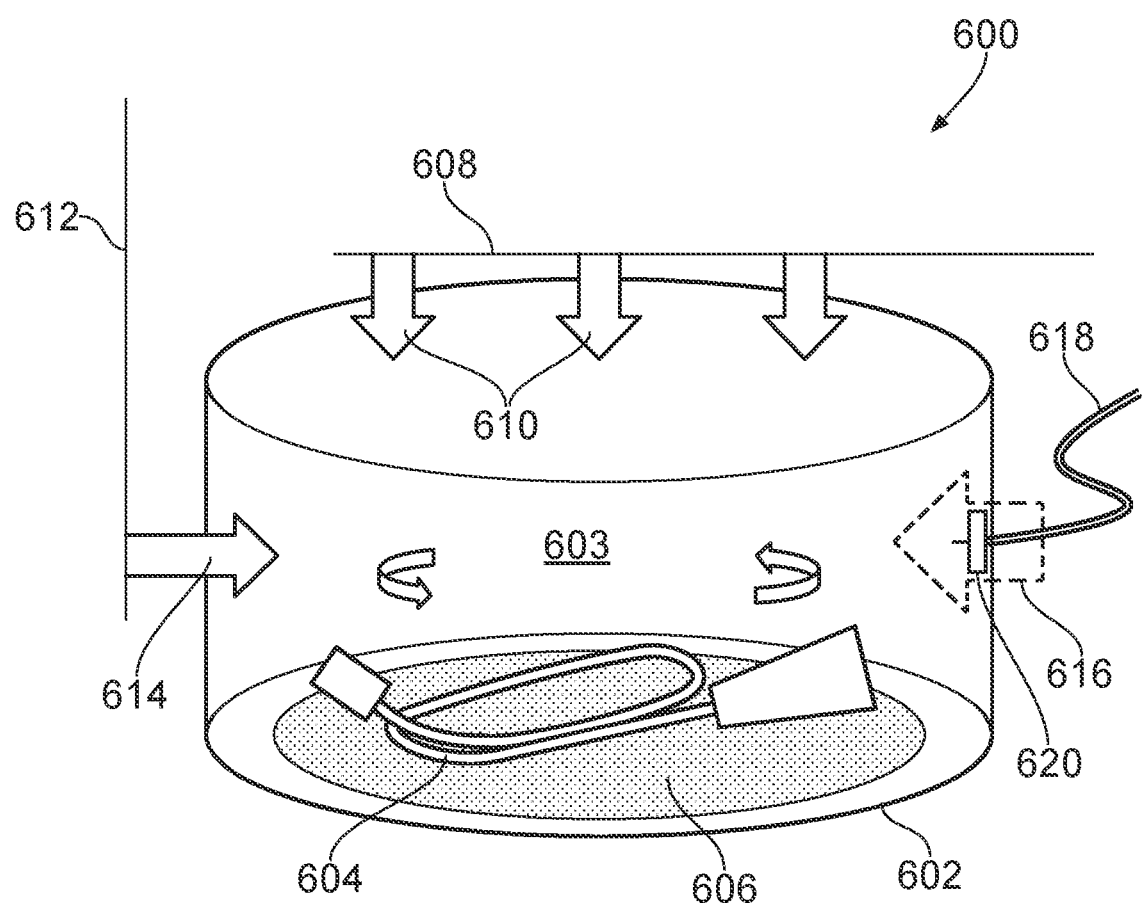
FIG. 14 is a schematic view of sterilization apparatus suitable for sterilizing an external surface of a surgical scoping device using the principles of the invention.

The apparatus may include a turntable or other rotation mechanism for rotating the scoping device within the internal volume to ensure that all regions of the outer surface are subjected to non-thermal plasma or OH radicals. An example of such an apparatus is shown in FIG. 14, discussed below.

The scoping device may be washed in a conventional industrial washing machine before it is subjected to sterilization. However, in another example, the sterilization apparatus may be integrated into a conventional industrial washing machine. For example, the drum of the washing machine may be configured as a microwave cavity into which microwave EM energy can be launched. Alternatively or additionally, plasma applicators such as those discussed above may be arranged around or on the drum to deliver plasma therein.

Figure 9:
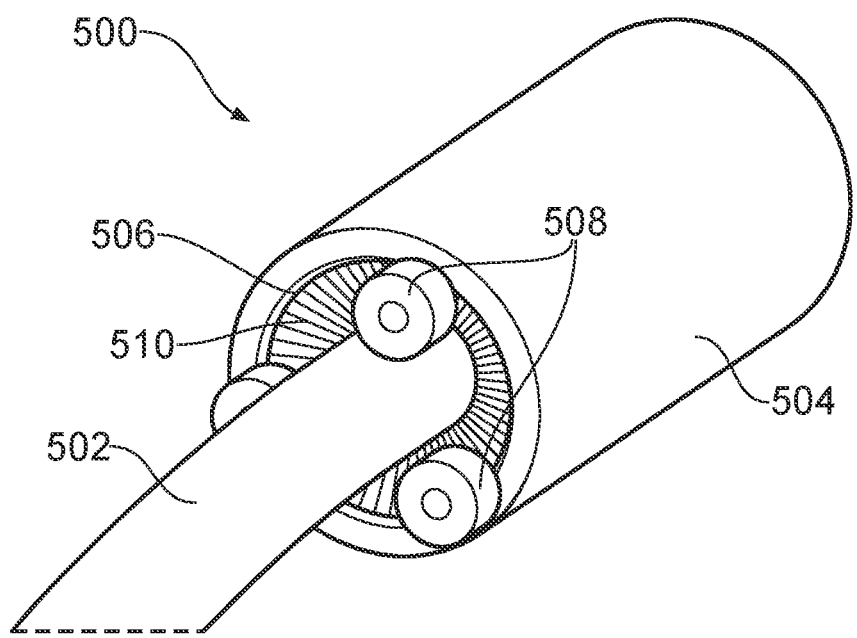
FIG. 9 is a perspective view of a distal end cleaning device that is an embodiment of the invention.

FIG. 9 depicts a distal end cleaning device 500 configured to clean and sterilise a distal end of a insertion tube 502. The distal end cleaning device 500 may be used in combination with the sterilization apparatus 10 and annular sterilization generator 308 discussed above, or may be standalone unit.

The distal end cleaning device comprises a housing 504, e.g. a rigid cylindrical housing, that defines a recess 506 dimensioned to receive a distal end of the insertion tube 502 of a surgical scoping device. The insertion tube 502 is supported by a plurality of rollers 508, which act to centre it within the recess 506. The recess 506 contains a brush 510, which spans across the recess to contact the distal end face of the insertion tube. The brush 510 is connected to a drive unit (e.g. linear or stepper motor, not shown) mounted in the housing 504. In use, the brush is rotated by the drive unit to clean the optics and any recesses in the distal end face of the of insertion tube 502.

In one example, the housing 504 may further comprise a plurality of brushes that extend around the side surfaces of the distal end of the insertion tube. These additional brushes may also be configured to rotate within the housing to clean the outer circumference of the insertion tube at its distal end. Such brushes may also be included within the annular plasma generator 308 discussed above.

In addition to the brushes, the housing may also comprise a plasma applicator (e.g. similar to the probe tip discussed above) mounted within the housing 504 to deliver non-thermal or thermal plasma source on to the distal end face of the insertion tube 502 for sterilization or disinfection. The housing 504 may also include a water inlet for introducing water or mist to aid the cleaning process and/or assist with the generation of hydroxyl radicals to sterilise the end of the scope.

Figure 10:
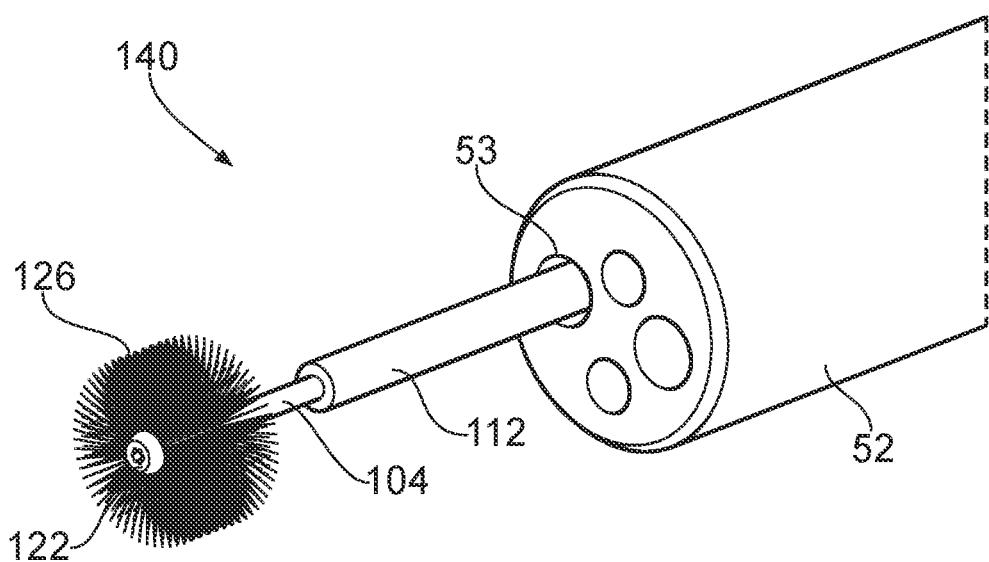
FIG. 10 is a perspective view of a probe tip having a brush that can be used with the present invention.

FIG. 10 depicts a probe tip 140 for a sterilization apparatus 10 similar to that discussed above with respect to FIG. 1, in which the elongate probe protrudes from the instrument channel 53 at the distal end of the insertion tube 52. Features in common with the probe tips discussed above are given the same reference number and are not described again.

The probe tip 140 includes a disc-like brush 126 mounted on a distal portion of the second electrode 104, proximal to the end cap 122. The brush may be deformable to fit through the instrument channel 53. It may be used to rub against the distal end face of the insertion tube 52 to assist in cleaning. The plasma or hydroxyl radicals for sterilisation may be generated within or proximally to the brush.

FIG. 11A depicts another probe tip 150 that can be used in the invention. Features in common with the probe tips discussed above are given the same reference number and are not described again.

In this example, the probe tip 150 is supplied with water through the elongate probe, and comprises a plurality of water outlet holes 152 formed in the second electrode 104.

FIG. 11B is a cross-sectional view through the probe tip 150. In this example, the inner conductor 108 of the coaxial cable 12 is hollow to define a longitudinal channel 151 for conveying water from a proximal end of the elongate probe to the probe tip. The first electrode 102 in this example comprises a distal portion of the inner conductor 108 that extends beyond a distal end of the coaxial cable 12. The longitudinal channel 151 continues into the first conductor 102. Within the plasma generating region 103, a outlet 156 (e.g. one of more radial holes through the first electrode 102) enables water to escape from the longitudinal channel 151. The outlet 156 may be configured as a nozzle to facilitate generation of a water mist within the space 103. The outlet holes 152 in the second conductor 104 allow the water to exit the probe tip and come into contact with the inner surface of the insertion tube (not shown).

The outlet holes 152 are located proximally to the gap at which plasma is emitted by the probe tip. Thus, when the device is withdrawn through the instrument channel, water mist can be supplied to the surface of the insertion tube just before the plasma is directed to that region. This may facilitate the generation of hydroxyl radicals for the purpose of sterilization or disinfection.

The probe tip may be used to deliver water only, e.g. to flush the channel, or to deliver plasma without water (e.g. a thermal plasma to dry the channel) or to deliver both plasma and water at the same time (e.g. to treat the instrument channel with hydroxyl radicals).

FIG. 12 depicts another probe tip 160 that can be used in the invention. Features in common with the probe tips discussed above are given the same reference number and are not described again. In this example, the end cap 122 is extended in a distal direction, and has a brush 162 mounted thereon. The brush may be configured for the same purpose a brush 126 shown in FIG. 10. In this example, the outlet holes 152 are located distally to the gap 119, within the brush 162. The delivered water is therefore for the purpose of facilitating the cleaning action of the brush 162.

FIG. 13 depicts another probe tip 170 that can be used in the invention. Features in common with the probe tips discussed above are given the same reference number and are not described again. The probe tip 170 is the same as probe tip 160 except that the outlet holes 152 are located proximally to the gap 119, and are for the same purpose as those disclosed in FIGS. 11A and 11B. It is to be understood that the probe tip may have any combination of the water outlet holes discussed herein.

FIG. 14 depicts a sterilization apparatus 600 configured to sterilize an external surface of a surgical scoping device 604. The apparatus 600 comprises a chamber 602, e.g. a cylindrical housing, that defines an internal volume 603 for receiving the surgical scoping device 604. The chamber 3602 may have a removable lid or other openable window or door to permit the surgical scoping device 604 to be inserted and removed.

The chamber 602 comprise a turnable 606 on which the surgical scoping device 604 is mounted. The turnable 606 is rotatable within the chamber 602, e.g. under the control of a drive mechanism (not shown) that can be located in a base of the chamber 602.

The internal volume 603 is arranged to receive a variety of inputs to assist in sterilizing the external surface of the surgical scoping device 604.

For example, a water supply 608 may be connected to deliver water to a plurality of water inlets 610 that inject water (e.g. as mist or spray) into the internal volume 603. In this example, the plurality of water inlets 610 are shown to be in a top surface of the chamber 602. However, in practice they may be located around any or all surfaces of the chamber, e.g. to deliver a uniform mist into the internal volume.

The chamber 602 includes a microwave inlet 616 from which microwave energy can be launched into the internal volume 603. The internal volume may be configured as a microwave cavity. The microwave energy may be conveyed to the chamber 602 by suitable cable 618 which terminates an a microwave coupler 620 which couples the microwave energy into the internal volume.

A gas supply 612 may be connected to the a gas inlet 614 for delivering gas, e.g. inert gas such as argon, into the internal volume. The combination of inert gas and microwave energy may permit a plasma to be struck in the internal volume. The presence of plasma and mist together may facilitate formation of hydroxyl radicals to assist with sterilization. Although not shown in FIG. 14, the gas inlet and microwave inlet may be combined so that plasma is injected directly into the chamber 602.

Additionally or alternatively, the chamber 602 may be arranged to receive a supply of ultraviolet (UV) radiation that can be delivered into the internal volume. The UV radiation may also assist in the formation of hydroxyl radicals from the water mist.

Other types of apparatus may be provided to sterilize the external surface of the surgical scoping device 604 using hydroxyl radicals. For example, an array of plasma jets (or possibly intense UV sources) may be used in conjunction with a mist generator to scan over or around the surgical scoping device 604.

The invention claimed is:

1. An apparatus for sterilizing a surgical scoping device, the apparatus comprising:
   a sterilization instrument insertable through a longitudinal channel that extends along an insertion tube of a surgical scoping device, the sterilization instrument comprising:
     an elongate probe comprising a coaxial cable for conveying radiofrequency (RF) electromagnetic (EM) energy or microwave EM energy,
     a probe tip connected at the distal end of the coaxial cable for receiving the RF or microwave energy, and
     a gas conduit for conveying gas to the probe tip;
   wherein the elongate probe comprises a protective sleeve that defines a lumen through which the coaxial cable extends, and wherein the gas conduit is an annular passageway formed between an outer surface of the coaxial cable and an inner surface of the protective sleeve,
   wherein the coaxial cable comprises an inner conductor, an outer conductor and a dielectric material separating the inner conductor from the outer conductor,
   wherein the probe tip comprises a first electrode connected to the inner conductor of the coaxial cable, and a second electrode connected to the outer conductor of the coaxial cable,
   wherein the second electrode encloses an internal volume of the probe tip, wherein the first electrode extends longitudinally within the internal volume,
   wherein the probe tip further comprises an insulating cap mounted at a distal end of the coaxial cable to isolate the coaxial cable from the internal volume,
   wherein the gas conduit is in fluid communication with the internal volume via a flow path formed between the insulating cap and the second electrode,
   wherein the first electrode and second electrode are configured to receive the RF or microwave energy from the coaxial cable to set up an electric field in the internal volume for striking a plasma therein,
   wherein the probe tip includes an outlet for releasing plasma from the internal volume,
   wherein the insulating cap is mounted within the second electrode,
   wherein the second electrode is a cylinder that sits within the annular passageway of the gas conduit at its distal end, and
   wherein the second electrode is castellated to provide a plurality of longitudinal notches in the cylinder that provide the flow path to permit gas flow around the insulating cap.

2. The apparatus of claim 1 including a liquid conduit for delivering water to the internal volume.

3. The apparatus of claim 2, wherein the liquid conduit is a hollow passage through the inner conductor of the coaxial cable.

4. The apparatus of claim 2, wherein the liquid conduit is configured to deliver water mist into the internal volume.

5. The apparatus of claim 1, wherein the probe tip comprises a conductive cap mounted on the first electrode at a distal end of the internal volume, the conductive cap being spaced from a distal end of the second electrode to define the outlet.

6. The apparatus of claim 1, wherein the first electrode is helical.

7. The apparatus of claim 1, wherein the first electrode is formed from a portion of the inner conductor of the coaxial cable that extends beyond a distal end of the outer conductor.

8. The apparatus of claim 1, wherein the insulating cap has a chamfered distal edge.

9. The apparatus of claim 1 further comprising a withdrawal device mounted on the elongate probe and configured to retract the elongate probe therethrough.

10. The apparatus of claim 9, wherein the withdrawal device comprises a motor drivable to retract the elongate probe at a speed less than 10 mm per second.

11. The apparatus of claim 1, wherein the probe tip further comprises a cleaning brush mounted at a distal end thereof.

12. The apparatus of claim 1 further comprising a vibration excitation device configured to impart ultrasonic vibrations to the elongate probe or the probe tip.

13. The apparatus of claim 12, wherein the vibration excitation device is mounted on the elongate probe.

* * * * *